United States Patent [19]

Amstutz et al.

[11] 4,261,062
[45] Apr. 14, 1981

[54] NATURAL SHOULDER JOINT PROSTHESIS

[75] Inventors: Harlan C. Amstutz, Pacific Palisades; Ian C. Clarke, Santa Monica, both of Calif.

[73] Assignee: The Regents of the University of California, Berkeley, Calif.

[21] Appl. No.: 22,689

[22] Filed: Mar. 22, 1979

[51] Int. Cl.³ .............................................. A61F 1/03
[52] U.S. Cl. ..................................... 3/1.91; 128/92 C
[58] Field of Search .................... 3/1.91, 1.912, 1.913; 128/92 C, 92 CA; 403/114, 122, 124, 125

[56] References Cited

U.S. PATENT DOCUMENTS

| | | | |
|---|---|---|---|
| 3,694,820 | 10/1972 | Scales et al. | 3/1.91 |
| 3,965,490 | 6/1976 | Murray et al. | 3/1.913 |
| 3,979,778 | 9/1976 | Stroot | 3/1.91 |
| 4,003,095 | 1/1977 | Gristina | 3/1.91 |
| 4,045,825 | 9/1977 | Stroot | 3/1.91 |
| 4,045,826 | 9/1977 | Stroot | 3/1.91 |
| 4,054,955 | 10/1977 | Seppo | 3/1.91 |
| 4,106,130 | 8/1978 | Scales | 3/1.91 |
| 4,141,088 | 2/1979 | Treace et al. | 3/1.912 |

FOREIGN PATENT DOCUMENTS

| | | | |
|---|---|---|---|
| 2400650 | 7/1974 | Fed. Rep. of Germany | 3/1.91 |
| 1362187 | 7/1974 | United Kingdom | 3/1.91 |
| 1470762 | 4/1977 | United Kingdom | 3/1.91 |

OTHER PUBLICATIONS

Krueger, "A Vitallium Replica Anthroplasty on the Shoulder," *Surgery* Dec., 1951, pp. 1005-1011.

Judet, et al., "Oblique Femoral Heads," *Journal of Bone and Joint Surgery*, vol. 36B, Nov. 1954, Adv. p. 18.
Bechtol, "Bechtol Total Shoulder," 6 pp., *Vitallium Surgical Appliances and Instruments*, Catalog of 1964, p. 55.

*Primary Examiner*—Clifford D. Crowder
*Attorney, Agent, or Firm*—Poms, Smith, Lande & Rose

[57] ABSTRACT

A complete shoulder joint replacement includes a metal ball and stem for securing at the upper end of the upper arm bone or humerus, with the shape of the ball being spherical at the top and of elliptical cross-section at the juncture with the surface of the upper arm bone; and a concave plastic prosthesis having a keel of generally elliptical cross-sectional configuration matching the shape of the corresponding glenoid recess in the scapula, or shoulder bone. The metal prosthesis which is secured in the upper arm or humerus has a rounded metal stem with a longitudinal rib to prevent rotation and three fins under the head to further assist fixation. The matching glenoid prosthetic replacement is elliptical, both at the articulating surface and within the glenoid recess, to conform to the natural shape of the joint. Fixation grooves encircle the fixation keel, and the keel may be clipped off at the fixation grooves to accommodate various depths of the glenoid recess in the scapula bone. The glenoid prosthesis may be either relatively open, which is the preferred configuration, or somewhat hooded, depending on the strength and development of the "rotator cuff," the musculature and associated ligaments and the like which hold the relatively unconstrained shoulder joint in position.

13 Claims, 9 Drawing Figures

NATURAL SHOULDER JOINT PROSTHESIS

FIELD OF THE INVENTION

The present invention relates to artificial shoulder joints.

BACKGROUND OF THE INVENTION

A number of different types of artificial shoulder joints have been proposed heretofore, and patent and other literature describing such joints will be set forth at a later point in the present specification. However, it appears that for the most part these artificial shoulder joints were based on some preconceived concepts of the designer of the joints and generally did not take into full consideration the exact anatomical configuration of the real human shoulder joint.

From an overall standpoint, the shoulder joint is relatively unconstrained. It includes a matching ball and socket, but the ball and socket members are held in their relative positions by a "rotator cuff" which includes a heavy layer of muscles and ligaments which surround the joint, and which also control the overall movement of the arm relative to the body. Although the shoulder has been referred to casually as a "non-weight-bearing joint," the compressive force acting on the shoulder joint reaches aproximetely 0.8 of body weight when the arm is raised horizontally, medically referred to as 90 degrees abduction, under static conditions. Accordingly, in the course of undertaking heavy work or athletic activities, the shoulder frequently carries loads substantially greater than the human body weight. Certainly, therefore, the shoulder, medically referred to as the glenohumeral articulation, is a major load-bearing joint.

Concerning terminology, the upper arm bone is the humerus, and the ball or rounded joint member at the upper end of the humerus fits into a socket in the shoulder bone, or scapula. the term "glenoid" refers to a pit or a socket, including that in the scapula which receives the ball at the upper end of the humerus. Accordingly, the shoulder joint is sometimes referred to as the glenohumeral articulation.

A number of the prior artificial shoulder joint proposals have involved fully constrained geometries. In such fully constrained geometries, at the limit of travel of the one joint element relative to the other, a positive stop is encountered, and the resultant forces between the arm and the shoulder must necessarily be applied to the joint between the prosthesis and either the humerus and the scapula or both, as the case may be. Unfortunately, the scapula is a relatively light bone, without the depth and massiveness required for very high strength securing of a prosthesis; accordingly, failure rates have approached 50% relative to the glenoid prosthesis in a number of the constrained joint configurations.

In other geometries which have been proposed, the precise shape of the humerus and/or the scapula in human beings has not been closely studied by the designer, so that the resultant joint does not provide a natural movement for the user, or the mode of securing is less than optimum because of the failure to match the prosthesis with the shape of the humerus, or the glenoid recess in the scapula, or both.

Accordingly, a principal object of the present invention is to provide a relatively unconstrained artificial shoulder joint conforming as far as possible to the configuration of the human body, both with regard to the configuration of the joint surfaces, and also with regard to the matching of each prosthesis with the bones to which they must be secured.

SUMMARY OF THE INVENTION

In accordance with the present invention, a metallic humeral shoulder joint prosthesis includes a stem for securing in the upper end of the humerus and a generally hemispherical ball having a surface which tapers to an elliptical cross-sectional configuration at the sides of the ball and at the lip where it is intended to engage the remaining portion of the humerus.

The metallic humeral prosthesis may also include an elongated stem having a generally circular cross-section, a smooth longitudinal rib to resist rotation, and three vanes or fins under the generally hemispherical head for increased fixation. Further, the underside of the generally hemispherical ball may be an extended flat surface or flange for mating with the upper end of the humerus.

The matching concave glenoid prothesis to be secured in the scapula is elliptical in configuration to conform to the natural shape of the shoulder joint, and has a spherical surface which generally matches that of the humeral prosthesis. The glenoid prosthesis is provided with a tapered keel, of elliptical cross-sectional configuration, to fit into and match the natural recessed form of the shoulder joint. Transverse fixation grooves encircle the fixation keel, and the keel may be clipped off at the fixation grooves to accommodate various depths of the recess in the scapula bone. The glenoid prosthesis may be either relatively open, which is the preferred configuration, or somewhat hooded, depending on the degree of musculature of the rotator cuff of the patient.

Several different sizes of humeral and glenoid prosthesis are provided to accommodate patients of different physical builds.

The humeral prosthesis is preferably formed of a special stainless steel, and the receiving cup or glenoid prosthesis is preferably formed of ultra-high molecular weight polyethylene.

The surgical procedure includes the initial steps of incision, exposure, and dislocation. The head of the humerus is then resected at 45 degrees to the shaft. The glenoid cancellous bone stock is excavated, preferably using a small high speed burr. The humeral canal is excavated, and this may be accomplished with a T-brach and rasp. The humeral and glenoid prostheses are subject to trial fittings with the proper size components, and a trial reduction is carried out. Following satisfactory fitting, the glenoid prosthesis and then the humeral prosthesis are cemented in place with suitable medical cement, such as radiopaque acrylic cement.

Advantages of the present technique include a more natural joint articulating surface configuration, permitting greater freedom of movement, and fixation configurations, for both the humeral and glenoid components, which conform closely to the configuration of the human anatomy, so that loosening of either of the prostheses is less likely than with prior proposed arrangements.

Other objects, features, and advantages of the invention will become apparent from a consideration of the following detailed description and from the drawings.

DETAILED DESCRIPTION

Figure 1:
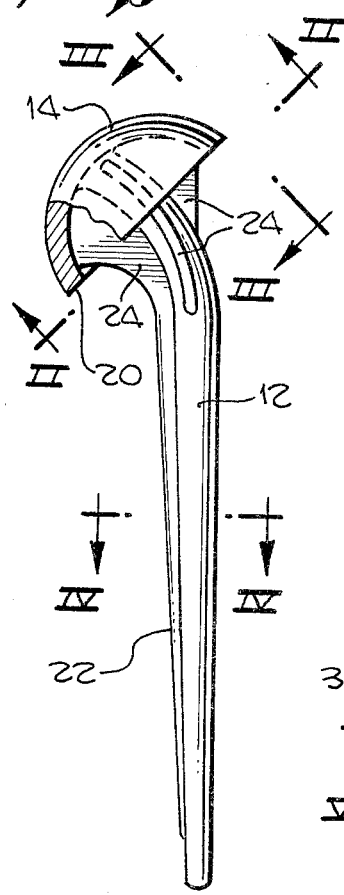
FIGS. 1 through 4 show various views of the metallic humeral prosthesis illustrating the principles of the present invention.
Figure 2:
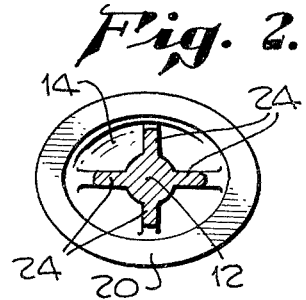
Figure 3:
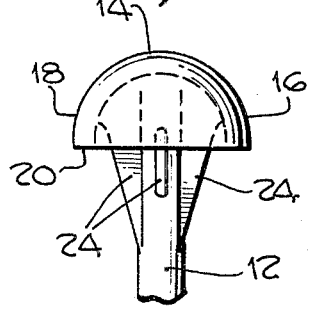

Referring more particularly to the drawings, FIG. 1 shows the metallic humeral prosthesis including an elongated stem 12 and a ball 14 which is offset and angled with respect to the central axis of the stem 12. The central portion of the ball 14 is spherical in its configuration. However, as indicated in FIGS. 2 and 3, the sides 16 and 18 are contoured, so that the cross-sectional configuration of the ball 14 adjacent the flange 20 which engages the remaining portion of the upper end of the humerus following resectioning, is elliptical in cross section.

Figure 4:
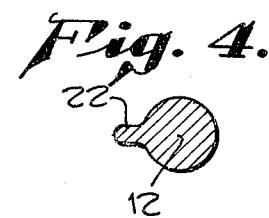

FIG. 4 is a cross sectional view of the stem taken along lines IV—IV of FIG. 1. FIG. 4 clearly shows the rouned rib 22 which extends outwardly from the main portion of the stem 12, and serves to resist rotation of the prosthesis within the central medullary canal of the humerus where it is mounted, as disclosed below.

The ribs or fillets 24 extend from the stem 12 to the inner surface of the head 14. They provide additional strength at the joint between the head 14 and the stem 12, and also assist in the fixation of the prosthesis to the upper end of the humerus. Table I set forth below gives the precise dimensions of the humeral prosthesis for each of three sizes. In practice, it has been determined that three sizes are adequate to fit the great majority of human body sizes.

TABLE I

DIMENSIONS OF HUMERAL PROSTHESIS
(millimeters)

| Identification of Part of Prosthesis | SIZE | | |
|---|---|---|---|
| | Large | Medium | Small |
| Spherical Diameter | 52 | 46 | 40 |
| Minor Axis Length | 48 | 42 | 36 |
| Height of Head From Flange | 25 | 20 | 15 |
| Offset of Axis of Flange From Stem Axis | 10 | 10 | 10 |
| Axial Length of Stem From Center of Flange | 140 | 140 | 140 |
| Radius of Curvature of Inner Fillet or Rib | 10 | 10 | 10 |
| Diameter of Stem at Start of Curvature | 11 | 9 | 7 |
| Diameter of Stem Just Before End | 9 | 7 | 5 |

By reference to Table I it may be observed that the large size prosthesis has an elliptical, or oval flange having a major axis length of 52 millimeters (aproximately equal to the spherical diameter), and a minor axis length of 48 millimeters. The height of the head from the flange is 25 millimeters as compared with the spherical radius of 26 millimeters, indicating that the head is nearly hemispherical. The center of the flange 20 is offset by 10 millimeters from the axis of the main portion of the stem 12. Further, the length of the stem 12 along its axis from its end to a point even with the center of the flange 20 is 140 mm. for the large size, and also for the other two sizes. The radius of curvature of the fixation fillet or rib 24 is 10 mm.; and the diameter of the stem tapers from about 11 mm. as it starts to curve, to about 9 mm., a few millimeters from its end. Similarly, the dimensions for the medium and small size humeral prostheses are given in the next two columns in Table I.

In further review of the figures set forth in Table I above, it may be noted that, for the largest size humeral prosthesis, the ratio of the minor to the major axis of the ellipse is 48/52, or 0.923. Similarly, the corresponding ratios for the medium and the small size prosthesis are 0.913, and 0.900, respectively. In accordance with the convention of referring to ellipses in terms of the angle having a sine function corresponding to the foregoing ratios, the ellipse for the larger size prosthesis may be designated as a 67 degree ellipse, that for the medium size prosthesis, a 66 degree ellipse, and that for the smaller size humeral prosthesis a 64 degree ellipse. In general, the precise elliptical or oval configuration of the ellipse is not critical, but it should be generally in the order of 65 degrees in order to closely replicate the configuration of the natural humeral portion of the shoulder joint.

Prior to designing the present complete shoulder joint, applicants made extensive measurements on 33 actual shoulders. The results of such measurements are set forth in Tables II and III set forth below, with Table II providing humeral data and Table III providing information relating to the glenoid cavity, with only 11 examples in which the glenoids were excavated as would be performed at surgery as contrasted with the 33 shoulder joints total which were measured. In the case of the glenoid cavity dimensions, the shape of the cavity was considered to be important. Accordingly silicone casts were made of the maximum space obtained within each of the 11 excavated glenoids. These replicas were then serially sectioned parallel to the glenoid surface at 3 millimeter increments and photographed, providing from 4 to 8 sections, depending on the glenoid depth. In Table III, the number 33 indicates that the articular surface of 33 glenoids were measured, while the numbers 11, the first 3 sections indicates that all 11 of the glenoids which were excavated had a depth of at least 9 millimeters (based on the successive 3 millimeter sections). Further, 10 of the 11 glenoid cavities extended beyond 12 millimeters in depth, and 9 beyond 15 millimeters in depth, as indicated by Sections 4 and 5.

TABLE II

HUMERAL ANTHROPOMETRIC DATA

| DIMENSION | MEAN DIMENSION OR ANGLE |
|---|---|
| Minimum canal dia. (L = 140 mm) | 12.8 ± 2.8 |
| Offset of head/neck junction (mm) | 10.3 ± 1.9 |
| Head thickness (mm) | 19.6 ± 5.2 |
| Humeral head major axis (mm) | 47.6 ± 9.0 |
| Humeral head minor axis (mm) | 43.7 ± 9.2 |
| Head radius (mm) | 24.3 ± 5.6 |
| Head-stem angle (degrees) | 135.5 ± 3.4 |
| Head retroversion (degrees) | 32.7 ± 5.4 |

TABLE III

REPLICATED GLENOID CAVITY DIMENSIONS

| Section Number | Number of Samples | Major Axis (mm) | Minor Axis (mm) | Ratio |
|---|---|---|---|---|
| Articular Surface | 33 | 40.5 ± 7.6 | 25.3 ± 8.3 | 0.62 |
| 1 | 11 | 22.3 | 17.9 | 0.8 |
| 2 | 11 | 21.1 | 12.3 | 0.6 |
| 3 | 11 | 22.3 | 10.1 | 0.5 |
| 4 | 10 | 21.8 | 7.6 | 0.4 |
| 5 | 9 | 16.8 | 5.9 | 0.3 |

Now, continuing with a description of the drawings, the glenoid or plastic cup prosthesis will now be considered.

Figure 5:
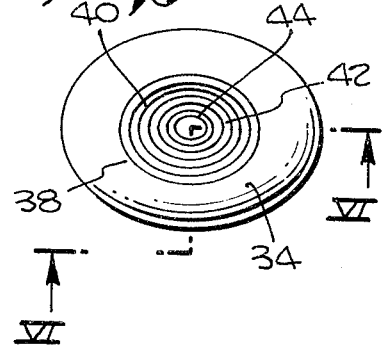
FIGS. 5 through 7 show various views of a glenoid prosthesis illustrating the principles of the present invention.
Figure 6:
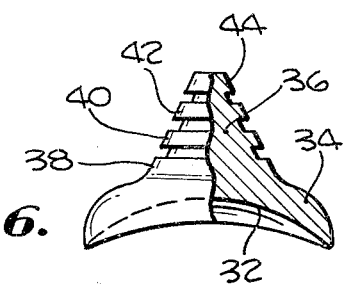
Figure 7:
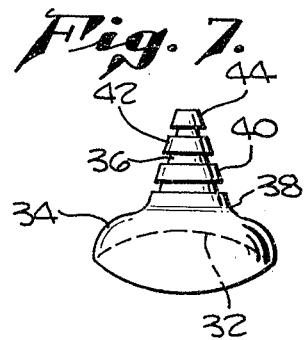

FIGS. 5, 6 and 7 illustrate one embodiment of the glenoid component which is configured to closely match the glenoid recess configuration as set forth in Table III. FIG. 6 is a side view with a partial cross section taken along the major axis of the elliptical configuration. The prosthesis includes the spherical surface 32 and immediately associated supporting material 34, and a rearwardly extending keel portion 36. The portion 34 is approximately 5 millimeters in thickness up to the transitions zone where it smoothly changes shape and merges into the keel 36.

Incidentally, the glenoid component is preferably made of ultra high molecular weight polyethylene, which has been found to be medically inert and non-reactive, when used as a prosthesis within the human body. Other medically inert materials may be employed which have a necessary strength and collateral properties. The keel 36 is provided with a series of transversly extending ribs 40, 42 and 44, with the keel terminating in the element 44. Each of these ribs elements is approximately 2 millimeters in depth and has a groove between it and the adjacent rib to assist in the fixation of the glenoid prosthesis by suitable medical cement.

FIG. 5 is a view of the prosthesis of FIG. 6 from the keel side, and clearly shows the overall elliptical configuration of the prosthesis conforming to the elliptical configuration of the glenoid recess. FIG. 7 is a side view of the prosthesis of FIG. 6 showing the reduced width of this component of the artificial joint in the other direction.

Figure 8:
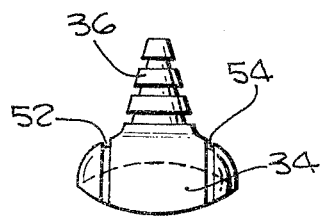
FIG 8 is a modified version of the glenoid prosthesis including additional fixation grooves.

FIG. 8 is a view of an alternative embodiment of the prosthesis of FIG. 6 which includes two additional fixation grooves 52 and 54 extending longitudinally with respect to the rear surface of the articulation surface supporting material 34.

Reference is now made to Table IV indicating the dimensions of the glenoid prosthesis in each of the three sizes in which it is fabricated.

TABLE IV

GLENOID PROSTHESIS
(All Dimensions in millimeters)

| SIZE | BEARING SURFACE | | | |
|---|---|---|---|---|
| | RAD/CUR | MAJOR | MINOR | DEPTH |
| LARGE | 26 | 40 | 29 | 5 |
| MEDIUM | 23 | 34 | 24.5 | 5 |
| SMALL | 20 | 28 | 20 | 5 |

| SIZE | KEEL | | | |
|---|---|---|---|---|
| | DEPTH | NO. OF F.G | TOP | BOTTOM |
| LARGE | 15 | 3 | 20/14 | 4/3 |
| MEDIUM | 15 | 3 | 18/13 | 4/3 |
| SMALL | 15 | 3 | 16/12 | 4/3 |

From Table IV it may be noted that the three sizes of the glenoid prosthesis are designated large, medium, and small. Referring momentarily to the large size, it may be noted that the radius of curvature of the spherical articulation surface 32 (see FIG. 6) is 26 millimeters. Further, the next 2 columns which are headed "MAJOR" and "MINOR" give the major and minor axis of the ellipse, forming the periphery of the articulation surface, and these dimensions are 40 millimeters and 29 millimeters, respectively. Also, the thickness of the supporting surface 34 is shown in the next successive column as being approximately 5 millimeters.

Turning to the lower section of Table IV several dimensions for the keel portion of the prosthesis are given. First in each case it may be noted that the depth of the keel is 15 millimeters. This means that the total depth from the deepest portion of the surface 32 to the bottom of the keel is 15 millimeters in addition to the 5 millimeter thickness of the main portion of the prosthesis which supports the articulating surface. In the next column the number of fixation grooves (F.G.) is the same in each case and is equal to 3. The general dimensions of the oval configuration of the keel are set forth in the next 2 columns, with the major and minor diameters of the ellipses being given. More specifically, for the large size, the base of the keel is an ellipse of approximately 20 millimeters major axis and 14 millimeters minor axis; and the bottom of the keel is elliptical in configuration and has a major axis of approximately 4 millimeters and a minor axis of approximately 3 millimeters.

Of course, in Table IV the next successive rows for the medium, and for the small glenoid prosthesis may be read in the same matter. In each case, the glenoid prosthesis keel has the three successive segments 40, 42 and 44 which are spaced apart by fixation grooves. It has been noted above that in some cases the depth of the glenoid cavity is limited. When the surgeon finds such a condition, it is a simple matter to cut off the last one of the segments such as segment 44, or even 2 segments, in order to fit the glenoid prosthesis precisely to the patient. Accordingly, both as to the overall size of the glenoid prosthesis which must match the humeral prosthesis in the radius of the articulation surface, as well as in the easy alteration of the depth of the keel on the glenoid portion of the joint, the unit is closely configured in accordance with anatomical considerations.

Figure 9:
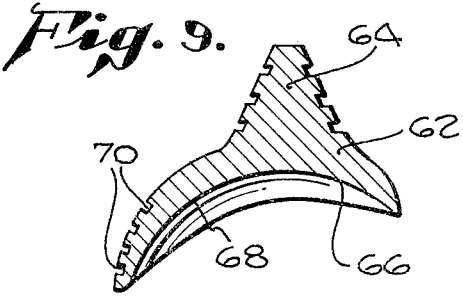
FIG. 9 shows an additional modified glenoid prosthesis including somewhat more constraint than that of other embodiments.

FIG. 9 is a cross sectional view of an alternative glenoid component 62 having a keel 64 and a spherical surface 66. The glenoid prosthesis of FIG. 9 differs from that of FIG. 6 in the partially hooded structure 68 which extends to the left, as shown in FIG. 9. This provides additional constraint for the joint, when the musculature of the rotator cuff of the patient is not sufficiently strong or well developed to fully support the joint. In order to assist in maintaining the glenoid prosthesis in place, additional fixation grooves 70 may be provided in the region near the hooded portion 68 of the unit. And these receive cement to hold the entire unit in place. These recesses may be in the order of 1.5 millimeters in width, and approximately 1 millimeter in depth.

For completeness, the operative technique will be briefly described in medical terms. Through an anterior saber-cut incision, the deltopectoral groove is enlarged and the tendon of subscapularis divided. The capsule is incised vertically and the joint is dislocated. If further exposure is needed, the anterior fibers of the deltoid muscle are elevated with a bone block from the clavicle. Using a template guide, the head of the humerus is resected at 45 degrees to the shaft and 40 degrees retroverted. A retractor which is pivoted on the posterior neck of the glenoid depresses the humerus posteriorly. All soft tissue is removed from the glenoid surface. The glenoid cancellous bone stock is excavated using a small high-speed burr. Care must be taken to protect the anterior wall, which is particularly vulnerable to penetration. Added anchorage holes may be added by hollowing out the coracoid process and if possible the axillary border of the scapula. The prepared glenoid cancellous bone bed is cleaned with a pulsating water lavage and dried with suction. The largest size glenoid prosthesis that will fit is chosen. The humeral canel is excavated with a T-brach and rasp. The humeral component corresponding with the chosen glenoid component is fitted and a trial reduction is carried out. Once a satisfactory fit has been obtained the glenoid and then the humeral component are cemented in place with radiopaque acrylic cement. After closure of the wound a swath and sling are applied. If the abductor mechanism has required repair after trauma, an abduction splint is applied for 6 weeks.

By way of background, it is noted that a related shoulder joint, which is similar in some respects to that disclosed herein, has previously been manufactured by Richards Manufacturing Company, 1450 Brooks Road, Memphis, Tennessee, 38116. The unit is described in a pamphlet entitled "Bechtol Total Shoulder", and the name of Dr. Charles O. Bechtol, MD, appears on the cover of the pamphlet. The prosthesis described in this pamphlet includes a fully spherical ball and stem metallic humeral prosthesis and a plastic glenoid prosthesis with a matching spherical articulation surface configuration.

As noted above, the Bechtol humeral prosthesis does not have an elliptical articulation surface in accordance with one of the features of applicants' invention, and the metal stem is irregular in shape and generally rectangular in cross-section in the portion which fits into the upper end of the humerus. This is in contrast with the stem of the humeral prosthesis as disclosed in the present specification which has a generally circular cross-sectional configuration, conforming to the shape of the medullary channel in the humerus. The flange of the spherical head is rounded and includes several openings. Concerning the glenoid portion of the joint, it has a rectangular base, instead of the elliptical keel of applicant's arrangments which conforms to the glenoid cavity geometry.

Concerning the elliptical configuration of the head of the humeral prosthesis, it is again noted that it is in the order of a 65 degree ellipse, with a range of from 55 degrees to 75 degrees being contemplated. Similarly, the plan configuration of the articulation surface of the glenoid prosthesis is in the order of a 45 degree ellipse, with the 0.725 ratio corresponding to about 46 or 47 degrees. However, the variations in the glenoid articulation surface dimensions, as indicated in Table III, provide substantial latitude. Concerning the elliptical configuration of the keel, it may be noted that the ratio of minor to major axis ranges from 0.8 to 0.3, from top to bottom of the glenoid cavity where the keel is to be positioned. If desired, the keel may be configured to precisely match this type of changing elliptical configuration. However, in the particular prosthesis for which dimensions are given in Table IV, a 45 degree ellipse, corresponding to a ratio of about 0.7 was employed as an approximation.

In conclusion, it is to be understood that the specific humeral and glenoid prosthesis described in the present detailed description and disclosed in the drawings are merely illustrative of the principles of the invention. Various modifications would also be within the scope of the invention, for example a different type of fixation recesses in the glenoid element, and minor departures in the fixation of the humeral prosthesis would still be within the scope of the invention, provided the principle of conforming to the actual geometry of the joint and adjacent bones is followed. Accordingly, the present invention is not limited to the exact construction shown and described herein.

What is claimed is:

1. A complete artificial shoulder joint conforming to the configuration of actual shoulder joints, comprising:
   a metallic humeral prosthesis including a tapered stem for mounting in the upper end of the humerus, and a generally hemispherical ball mounted at one end of said stem offset and at an angle of approximately 45 degrees with respect to said stem, said ball having a spherical configuration at the center and being smoothly reduced on each side to an elliptical cross-sectional configuration at the edge of said ball, where said ball is to engage the humerus; and
   a glenoid prosthesis formed of a high density medically inert plastic, including a surface body portion less than 10 millimeters thick, and having a concave bearing surface for engaging the ball of said humeral prosthesis, and having integral keel means of reduced cross-section mounted away from the edges of said surface body portion and having a linear extent less than three-quarters of the extent of the bearing surface, said keel means being of generally elliptical or oval cross-sectional configuration and being tapered to conform to the natural shape of the glenoid recess, for holding said glenoid prosthesis in place.

2. A complete artificial shoulder joint as defined in claim 1 further comprising a plurality of fixation recesses extending peripherally around said keel, whereby portions of said keel may be clipped off to conform the depth of said keel to the actual depth of the glenoid recess of the patient.

3. A complete shoulder joint as defined in claim 1 wherein said stem has a generally circular cross-sectional configuration, and is provided with a longitudinally extending rounded rib for resisting rotation of said stem; wherein said ball is provided with a flat flange on its under surface for engagement with the resectioned upper end of the humerus; and further comprising a plurality of fillets or ribs extending from said stem to the inner surface of said ball, said fillets or ribs extending below the flange of said ball to assist in the fixation of said humeral prosthesis.

4. A complete artificial shoulder joint as defined in claim 1 wherein the elliptical configuration of said ball is in the order of a 65 degree ellipse.

5. A complete artificial shoulder joint as defined in claim 1 wherein the elliptical cross-sectional configuration of said keel corresponds substantially to a 45 degree ellipse.

6. A glenoid shoulder joint prosthesis comprising a high density medically inert plastic, and including a surface body portion less than 10 millimeters thick, and having a concave bearing surface for engaging the ball of a humeral prosthesis, and having integral keel means of reduced cross-section mounted away from the edges of said surface body portion and having a linear extent less than three-quarters of the extent of the bearing surface, and said keel means being of generally elliptical or oval cross-sectional configuration conforming to the natural shape of the glenoid recess, for holding said glenoid prosthesis in place.

7. A glenoid should joint prosthesis as defined in claim 6 further comprising a plurality of fixation recesses extending peripherally around said keel, whereby portions of said keel may be clipped off at said fixation recesses to conform the depth of said keel to the depth of the glenoid recess of the patient.

8. A method of total shoulder joint replacement conforming to the natural anatomical configuration of the human body comprising:
performing joint an incision to expose the shoulder joint;
dislocating the shoulder joint to expose the damaged or diseased surface of the joint;
reacting the convex portion of the shoulder joint at an angle of approximately 45 degrees relative to the shaft of the humerus;
excavating the glenoid cavity below the normal articulation surface, to provide a tapered recess, of elliptical cross-sectional configuration conforming substantially to the natural configuration of the glenoid cavity;
cleaning and drying the glenoid cavity;
selecting a glenoid prosthesis formed of high density medically inert plastic, including a surface body portion less than 10 millimeters thick, and having a concave surface for engaging the ball of a humeral prosthesis, and having a tapered keel of reduced cross-section mounted away from the edges of said surface body portion and having a linear extent less than three-quarters of the extent of the bearing surface, and said keel means being of elliptical cross-section, of the largest size which will fit the excavated glenoid recess, said selecting step being made from at least three preformed different sizes;
excavating the medullary canal of the humerus;
selecting a humeral prosthesis having a generally hemispherical head matching the curvature of the selected concave glenoid prosthesis, said head being tapered to elliptical cross-sectional configuration at the two sides of said head;
cementing said glenoid and said humeral prostheses into the glenoid cavity in the scapula, and into the canal of the humerus, respectively; and
reducing the joint and closing the incision.

9. A method as set forth in claim 8 further comprising preparing additional anchorage recesses in the glenoid cavity to insure fixation.

10. A method as set forth in claim 8 further comprising engaging fillets or fins extending from the head to the stem of said humeral prosthesis with the upper end of the resected humerus to improve fixation.

11. A method as set forth in claim 8 in which the glenoid prosthesis selecting step includes the selection of a glenoid prosthesis in which the keel has a series of peripherally extending grooves, including the additional step of cutting off one or more segments of said keel at said grooves to fit the excavated glenoid recess, and wherein the cementing step includes cementing a thin uniform layer of cement between the inner surfaces of the glenoid prosthesis and the walls of the glenoid cavity.

12. A complete artificial shoulder joint comforming to the configuration of actual shoulder joints, comprising:
a metallic humeral prosthesis including a generally hemispherical ball, said ball having a spherical configuration at the center and being smoothly reduced on each side to an elliptical cross-sectional configuration at the edge of said ball, where said ball is to engage the humerus, and means for securing said ball to the upper extremity of the humerus;
a glenoid prosthesis formed of a high density medically inert plastic, including a surface body portion less than 10 millimeters thick, and having a concave surface for engaging the ball of said humeral prosthesis, and having integral keel means of reduced cross-section mounted away from the edges of said surface body portion and having a linear extent less than three-quarters of the extent of the bearing surface, and said keel means being of generally elliptical or oval cross-sectional configuration conforming to the natural shape of the glenoid recess, for holding said glenoid prosthesis in place.

13. A glenoid shoulder joint prosthesis comprising a high density medically inert plastic, including (1) a surface body portion approximately one-half centimeter in thickness, having a concave bearing surface for engaging the ball of a humeral prosthesis, (2) having integral keel means of reduced cross-section mounted away from the edges of said surface body portion and having a linear extent less than three-quarters of the extent of the bearing surface, and said keel means being of substantially elliptical or oval cross-sectional configuration conforming to the natural shape of the glenoid recess, for holding said glenoid prosthesis in place, said keel means having a depth at least twice that of the thickness of said surface body potion, and also including a plurality of full peripheral fixation grooves extending all of the way around said keel, whereby successive sections may be readily clipped off at said grooves, and the transverse linear extent of said keel at its extreme end being substantially less than one-half its transverse linear extent adjacent said surface body portion.

* * * * *